United States Patent [19]

Walz et al.

[11] 4,257,270

[45] Mar. 24, 1981

[54] ULTRASONIC IMAGING APPARATUS

[75] Inventors: Alfred Walz, Burgthann; Adalbert Birk, Erlangen, both of Fed. Rep. of Germany

[73] Assignee: Siemens Aktiengesellschaft, Berlin & Munich, Fed. Rep. of Germany

[21] Appl. No.: 948,147

[22] Filed: Oct. 3, 1978

[30] Foreign Application Priority Data

Oct. 21, 1977 [DE] Fed. Rep. of Germany ....... 2747405

[51] Int. Cl.³ .............................................. G01N 29/00
[52] U.S. Cl. ...................................... 73/620; 128/660
[58] Field of Search ................................. 128/660–663; 73/618–628, 631, 642; 328/142–145; 340/5 MP, 793; 358/21 R, 32, 112, 164, 244, 130–132, 166, 169; 307/350, 362–364

[56] References Cited

U.S. PATENT DOCUMENTS

| | | | |
|---|---|---|---|
| 2,884,484 | 4/1959 | Deichert | 358/164 |
| 3,458,652 | 7/1969 | McMann | 328/143 |
| 3,535,443 | 10/1970 | Rieke | 358/166 |
| 3,588,338 | 6/1971 | Dischert et al. | 358/164 |
| 3,633,044 | 1/1972 | Buckstadt | 328/142 |
| 3,716,297 | 2/1973 | Wakabayashi | 358/244 |
| 3,734,086 | 5/1973 | Phelps, Sr. | 128/200 |
| 3,996,420 | 12/1976 | Geluk | 358/244 |
| 4,045,815 | 8/1977 | Griffith et al. | 128/712 |
| 4,092,867 | 6/1978 | Matzuk | 128/660 |
| 4,106,346 | 8/1978 | Matzuk | 128/660 |

OTHER PUBLICATIONS

Hill, "Ultrasonic Imaging", *Journal of Physics* E (Scientific Instruments), vol. 9, No. 3, Mar. 1976 pp. 153–162.
Kossoff, G. "Improved Techniques in UTS Cross-Sectional Echography", Ultrasonics, vol. 10, No. 5, Sep. 1972 pp. 221–227.
Freeman, K. G. et al., "Variable Gamma Corrector Improves Television Video Signals", Electronic Engrng., vol. 42, No. 511, Sep. 1970, pp. 90–93.
Hill, C. R. et al., "UTS Echo Imaging of Tissues: Instrumentation" Brit. Jrnl. Radiology, vol. 49, No. 579, pp. 238–243, Mar. 1976.
Mountford, R. A. et al., "Semi-Automatic Transducer Movement for Ultrasonic Compound B-Scanning," Med. & Biol. Engrg., vol. 12, No. 6, Mar. 1974.

*Primary Examiner*—Robert W. Michell
*Assistant Examiner*—Francis J. Jaworski
*Attorney, Agent, or Firm*—Hill, Van Santen, Steadman, Chiara & Simpson

[57] ABSTRACT

In an illustrative embodiment, an ultrasonic receiver supplies the echo signals with a given dynamic range to an image recording device which manifests a non-linear luminance/control characteristic. An imaging apparatus with a signal transmission chain of such a type is to be produced with which, by simple means, the echo dynamic range can be adapted to the luminance range detectable by the eye. This is achieved in that there is connected between the ultrasonic receiver and the image recording device, a distortion member, particularly a linearization member, which distorts, in particular, linearizes, in accordance with a specifiable pattern, the non-linear luminance/actuating characteristic of the recording device, in dependence upon a predetermined optimum dynamic range of the echo signals.

4 Claims, 5 Drawing Figures

ULTRASONIC IMAGING APPARATUS

BACKGROUND OF THE INVENTION

The invention relates to an ultrasonic imaging apparatus for ultrasonic-echo recording according to the impulse-echo-principle, comprising ultrasonic transmitter/receiver which delivers echo signals with a specified dynamic range, as well as comprising an image recording device for the echo signals which manifest a non-linear luminance/control-characteristic.

In addition to the surface contours of the organs and vessels, the ultrasonic imaging process also effects the representation of the fine structures within the organs and vessels. The quality of an ultrasonic image is not only determined by the physical point-resolution in the ultrasonic beam; on the contrary, it is also influenced by the type of amplitude reproduction on the viewing screen of the oscilloscope tube or on the photographic medium for a photographed visual image. Echo signals which differ in their amplitude are represented on the viewing screen as image points of varying luminance. Luminance differences are perceived correspondingly by the eye of the observer as differences in the grey value. The amplitudes of the echoes received from the interior of the body comprise a dynamic range of more than 100 dB ("maximum echo contrast"). The structure-echoes, occurring as the result of diffuse scattering, are here distinguished by their smaller amplitude from the contour echoes, largely produced by means of specular (or direct) reflection, which manifest, without exception, a greater amplitude. Contrasting with the echo dynamic range of approximately 100 dB, there is a dynamic range of the luminance of only a maximum of 30 dB which the adapted eye of the observer can resolve into grey values between black and white ("maximum image contrast"). According to the Weber-Fechner-law, the eye evaluates the luminance perceived within this range logarithmically. The smallest difference in luminance which still can be distinguished by the eye is the threshold contrast $d_0$; it amounts to $d_0 = 0.83$ dB. Accordingly, the adapted eye of the observer resolves the 30 dB-range into approximately 35 grey steps. These sensory-physiological factors are of significance for ultrasonography in two respects. On the one hand, the eye can detect only a segment of the great echo dynamic range. This segment can be selected with the aid of a gain control, and the size (or magnitude) of the segment can be influenced by means of dynamic compression. On the other hand, the structure-resolution in the ultrasonic image is not solely determined by the physical lateral resolution defined as the half-width (width at one half maximum intensity) of the echo signal of a point-object; on the contrary, it is also influenced by the threshold contrast of the grey value resolution. Thus, e.g. two point-objects with the lateral spatial interval (or spacing) A in the ultrasonic image can be distinguished from one another as long as $d_1 - d_2$ is equal to or greater than $n \cdot d_0$, with $d_0 = 0.83$ dB, where $d_1$ is the echo signal which results when one of the two objects is disposed on the beam axis, and $d_2$ is the corresponding signal, given an interval $A/2$ of both objects from the beam axis; and where n is the compression factor for the instance of a dynamic compression of the form: luminance $\sim$ (echo amplitude)$^{1/n}$. Instead of the $(-6$ dB)-width of the echo signal of a point object, the lateral resolution is accordingly given by the $[-6-(n \cdot 0.83)]$dB-width. This definition of the point resolution is only valid and invariant, e.g. with respect to the choice of the echo amplification, as long as the relationship between echo amplitude and luminance is linear, or if said relationship follows the above-indicated exponential function. The definition loses its validity when the transmission system follows a function deviating therefrom; for example, a logarithmic function.

SUMMARY OF THE INVENTION

It is the object of the present invention to provide an ultrasonic imaging apparatus comprising a signal transmission chain of a type wherein the echo dynamic range can be adapted, in a simple fashion, to the luminance range detectable by the eye.

Taking into account the above-cited considerations, the object is achieved by virtue of the fact that there is connected between the ultrasonic receiver and the image recording device, a distortion member, particularly a linearization member, which distorts, particularly, linearizes, according to a predetermined pattern, the non-linear luminance/actuating (input)-characteristic of the recording device, in dependence upon a specifiable optimum dynamic range of the echo signals.

In a preferred embodiment of the invention, the distortion member is a so-called gamma-correction member which manifests a characteristic which is inverse in relation to the characteristic of the recording device. In this manner, e.g. in utilizing a television picture tube, the dynamic expansion of the tube can be compensated such that there corresponds to an echo dynamic range, already restricted by the receiving amplifier to 30 dB, a maximum luminance range of likewise 30 dB. In a further advantageous embodiment, in addition, there is to be series connected to the distortion member a threshold control which, in dependence upon a predetermined threshold voltage which lies above interference echoes which are to be eliminated, transmits those signal amplitudes which exceed the threshold voltage for further processing, in such a fashion as to be true-to-intensity, however, with suppression of the interference echoes. A threshold control such as this thus permits the elimination of small interference echoes, whereby, however, useful echoes which lie above the threshold of the threshold control remain entirely untouched in their amplitude and thus also in the echo grey value representation in the visual image.

Further advantages and details of the invention shall be apparent from the following description of a sample embodiment on the basis of the drawing in conjunction with the sub-claims; and other objects, features and advantages will be apparent from this detailed disclosure.

DETAILED DESCRIPTION

Figure 1:
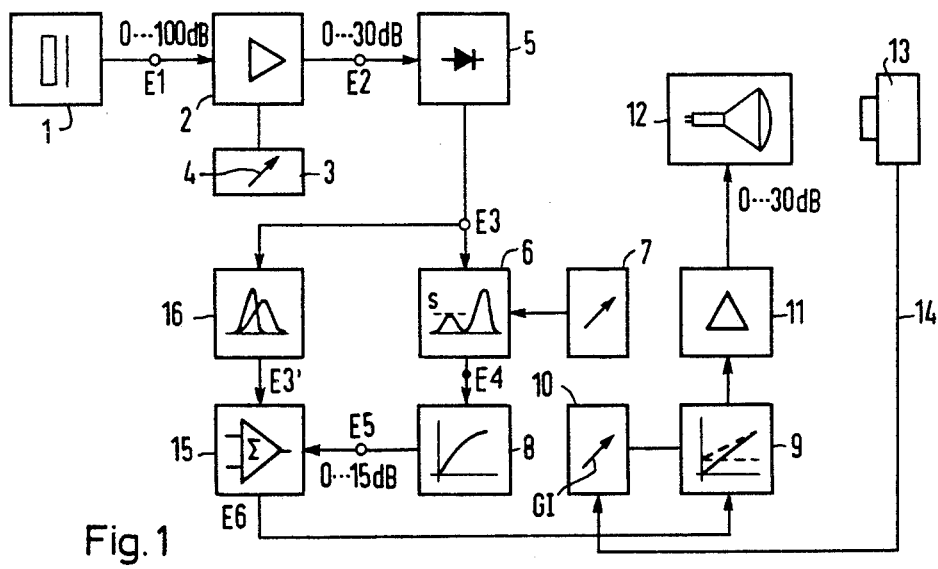
FIG. 1 illustrates the signal transmission chain of an ultrasonic imaging apparatus in a basic circuit diagram with a linearization member as the distortion member.

In FIG. 1, an ultrasonic transducer for the emission of ultrasonic pulses and for the reception of the echo pulses is referenced with 1. Transducer 1 can be a rotating transducer which, in conjunction with a paraboloid reflector, renders possible a linear scanning of an examination subject. However, an ultrasonic array can also enter into consideration, wherein a plurality of adjacently arranged ultrasonic transducers serves the purpose of linear subject-scanning. It can likewise also be a transducer for compound-scan or A-scan operation. The echo signals E1, received by transducer 1, which manifests an echo dynamic range of 0 up to approximately 100 dB, are amplified by means of echo signal amplifier or receiver 2 and simultaneously restricted to a dynamic range of 0 to 30 dB. The gain control 3 with adjustment member 4 serves the purpose of adjusting echo signal amplifier 2 to provide a desired degree of amplification. The dynamic-restricted echo signals E2 at the output of echo signal amplifier 2 are demodulated by means of rectifier 5 (diode rectifier), and the demodulated signal E3 is transmitted to a threshold control 6 with a threshold adjustment member 7. The threshold control 6 suppresses small interference echoes lying beneath the threshold S. Useful echoes which exceed the threshold, however, are allowed to pass through undistorted in their amplitude. Accordingly, an echo signal E4 occurs at the output of the threshold control 6 from which small interference echoes have been entirely eliminated. The echo signal E4, processed in this fashion, is finally transmitted to a gamma-correction member 8, which manifests a characteristic inverse to the gamma-curve of the picture tube 12. Through the compensation, the dynamic range of echo signal E4 is restricted to maximally 15 dB, and there thus results, due to the square (or quadratic) progression of the characteristic curve of the picture tube, a maximum luminance range of 30 dB. If the echo signal restricted to 30 dB were utilized directly for the purpose of beam current control of the picture tube, the corresponding luminance-dynamic range—i.e., the maximum image contrast—would amount to 60 dB on account of the square (or quadratic) characteristic curve (gamma-curve) of the tube. However, as already explained initially, this contrast cannot be resolved by the human eye. By means of interconnecting the gamma-correction member 8, however, the dynamic expansion of the tube is fully compensated such that there corresponds to the original 30 dB-range of the echo signal E2 at the output of the receiving amplifier 2, or E3 at the output of the demodulator 5, respectively, a maximum luminance range of likewise 30 dB at the picture tube image.

However, the human eye can resolve the luminance range of 30 dB only if its state of adaptation is not disturbed by surrounding field conditions. If the surrounding field-luminance (room brightness) is greater than the maximum luminance on the viewing screen, the overall contrast for the eye is too great. In this instance, the basic luminosity (or brightness) must be raised, and the maximum image contrast reduced. Specifically for the purpose of contrast adjustment, a contrast control 9 with a contrast adjustment member 10 is thus provided. The echo signal contrast-regulated in this fashion, is then transmitted via a video output amplifier 11 to the picture tube 12. The contrast control 9 is conceived such that it guarantees a linear dynamic adaptation of the echo signal to the maximum image contrast detectable by the eye. In this manner, the image at picture tube 12 can be adjusted to the optimum grey value reproduction for the eye. The optimum adjustment of the basic luminosity (or brightness) is achieved if the lowest grey step can just barely still be recognized. Thus, by means of contrast control it is guaranteed that, independent of the adjusted basic luminosity, all grey stages can be resolved.

The described contrast control is of particular significance for photo documentation with the aid of a photo attachment 13 (polaroid camera). This photo attachment 13 is connected, in the triggering mechanism, via signal control line 14, with the adjustment member 10 for the contrast control 9. If the triggering mechanism of the photo attachment 13 is actuated, the basic luminosity on the contrast control 9 is correspondingly adjusted to higher values via the adjustment member 10. The adjustment is such that basic luminosity and image contrast are adjusted to the maximum contrast of the utilized film material. With this type of contrast control, a clearly reproducible photo-image quality is guaranteed independently of how the image observer has previously individually adjusted the image on the viewing screen observed by him.

In the basic circuit diagram of FIG. 1, the echo signals E5 at the output of the gamma-correction member 8 are not directly transmitted to the contrast control 9. On the contrary, this signal E5 is first conveyed to a mixing stage 15 in which a signal E3' is superimposed on signal E5, said signal E3' resulting from the differentiation of echo signal E3 (at the output of demodulator 5) by means of differentiation stage 16. The differentiated signal E3' is superimposed on the signal E5 with a somewhat increased luminance on the viewing screen of the picture tube 12, which leads to an increase in the echo signal slopes in the picture. Through a suitable mixing of the differentiated and non-differentiated signal in the mixing stage 15, a sharper representation of the organ contours is thus rendered possible without impairing the grey value representation of the structure-echoes.

Figure 2A:
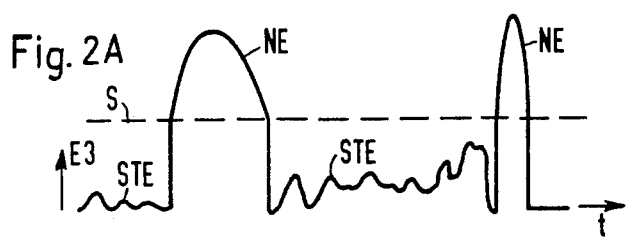
FIG. 2A showing an exemplary input waveform and FIG. 2B showing the corresponding output waveform.
Figure 2B:
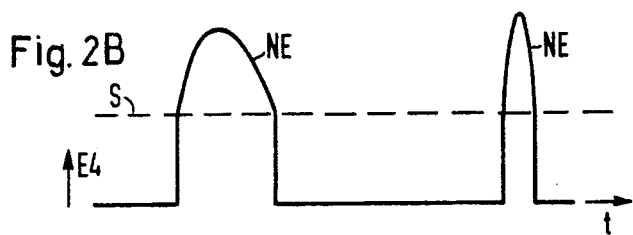
FIG. 2 illustrates a sample embodiment of the threshold control.
Figure 4:
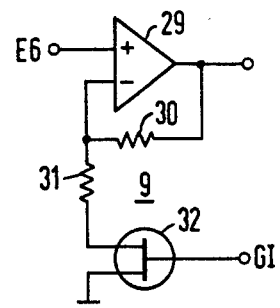
FIG. 4 illustrates a contrast control for the image contrast at the picture tube.
Figure 2:
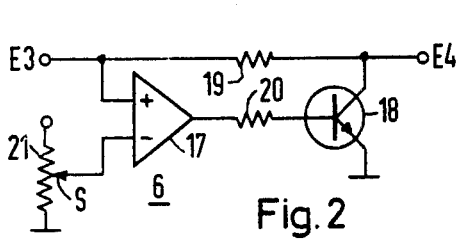
Figure 3:
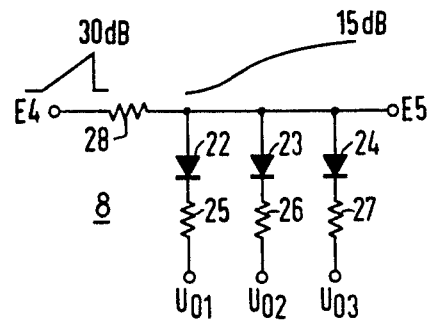
FIG. 3 illustrates an embodiment of a linearization member.

Sample embodiments for threshold control 6, gamma-correction member 8, and contrast control 9 are illustrated in FIGS. 2 through 4. In FIG. 2, the threshold control, in the simplest fashion, consists of comparator 17 with switching transistor 18. The components 19 and 20 are wiring resistances. By means of a potentiometer 21, the threshold voltage S of the threshold control can be adjusted. Potentiometer 21 thus corresponds to the threshold adjustment member 7 of FIG. 1. The method of operation of the example of FIG. 2 shall be apparent in conjunction with the exemplary input and output echo signal waveforms as a function of time illustrated in FIGS. 2A and 2B, as follows: The echo signal E3, FIG. 2A, arriving from demodulator 5 is constantly compared in comparator 17 with the threshold S. As long as the signal E3 lies below threshold S in its amplitude, transistor 18 is conductive such that the interference echoes STE of small amplitudes are completely short-circuited. However, if a useful signal component NE exceeds threshold S, transistor 18 is blocked such that the waveform E4 (t), illustrated therebelow in FIG. 2B, results. It is immediately apparent that the interference echoes STE, FIG. 2A, are suppressed, whereby, however, the amplitude of the useful echoes NE, independently of the threshold value S, has remained the same. What is achieved thereby is that echoes lying above the threshold S remain unaffected in the grey value representation on the picture tube.

In FIG. 3, the gamma-correction member 8 consists, in the simplest fashion, of a parallel-connection of semiconductor diodes 22, 23, and 24, in connection with ohmic resistances 25 through 28, as well as bias voltages UO1, UO2, and UO3. The bias voltages UO1, UO2, UO3 are stepped such that, in the case of a linear rise of the echo signal E4 over the range 0 to 30 dB, a root function curve results over the range 0 to 15 dB, due to the different voltage steps in which the diodes become successively conductive. Thus curve is inverse in relation to the gamma characteristic of the picture tube 12.

However, contrast control 9 according to FIG. 4, in turn, consists of an operational amplifier 29 with the wiring resistances 30 and 31. A field effect transistor 32, which acts as a variable resistance, is subjected to the control signal for the basic luminosity GI. In the case of normal contrast control, this signal GI can be directly adjusted at adjustment member 10 by means of an adjusting knob. In the case of a photographic exposure, however, the connecting-up of the signal GI via the signal control line 14 takes place upon triggering of the photographic exposure on photographic apparatus 13. Depending upon the choice of the adjustment value GI for the basic (or fundamental) luminosity, transistor 32 is more or less conductive. Not only a change in the basic luminosity results as a consequence of this; on the contrary, the linear dynamic adaptation of signal E6 to the maximum image contrast detectable by the eye also proceeds automatically via the operational amplifier 29.

With respect to the automatic operation of contrast control 9, FIG. 4, in response to triggering of photo installation 13, the manual adjustment 10 may take the form of a potentiometer (such as that at 21, FIG. 2) supplied by a high impedance source, and having its selected output potential supplied to terminal GI so as to control the effective resistance of transistor 32 when the photo installation 13 is inactive. The actuation of the trigger for installation 13 may connect a second potentiometer in parallel across terminal GI via control line 14 so as to instantaneously modify the effective resistance of transistor 32 upon actuation of the trigger. The second potentiometer may provide a low impedance source directly connected via line 14 to terminal GI when the trigger is actuated so as to essentially override the effect of the variable setting of the manual setting potentiometer 10. In this case, the minimum resistance value of the manual setting potentiometer 10 must greatly exceed the internal resistance of the low impedance source associated with control line 14.

It will be apparent that many modifications and variations may be effected without departing from the scope of the novel teachings and concepts of the present invention.

We claim as our invention:

1. Ultrasonic imaging apparatus for ultrasonic-echo recording according to the impulse-echo principle, comprising an ultrasonic receiver which delivers the echo signals with a given dynamic range, an image recording device for the echo signals which manifests a non-linear output/input characteristic, a distortion circuit (8) connected between the ultrasonic receiver (2) and the image recording device (12) which distortion circuit distorts, according to a specifiable pattern, the non-linear characteristic of the recording device (12), in dependence upon a predeterminable optimum dynamic range of the echo signals, and a threshold control circuit (6) connected in series with said distortion circuit (8), and having means whereby the threshold control circuit (8) has a specifiable threshold voltage (S), which lies above the amplitude of the interference echoes (STE), and is operable to transmit to said distortion circuit (8) such signal amplitudes (NE) which exceed the threshold voltage, and said threshold control circuit being operable to transmit said signal amplitudes (NE) which exceed the threshold voltage true-to-intensity, while the interference echoes are suppressed, characterized in that the threshold control circuit comprises a comparator (17) with an associated switching transistor (18), whereby the transistor (18), in the case of signals (E3) beneath the threshold adjusted at the comparator, forms a short-circuit for the input signal (E3), which, however, is canceled as soon as the incoming signal (E3) exceeds the threshold (S) in amplitude.

2. Ultrasonic imaging apparatus for ultrasonic-echo recording according to the impulse-echo principle, comprising an ultrasonic receiver which delivers the echo signals with a given dynamic range, an image recording device for the echo signals which manifests a non-linear output/input characteristic, a distortion circuit (8) connected between the ultrasonic receiver (2) and the image recording device (12) which distortion circuit distorts, according to a specifiable pattern, the non-linear characteristic of the recording device (12), in dependence upon a predeterminable optimum dynamic range of the echo signals, and a threshold control circuit (6) connected in series with said distortion circuit (8), and having means whereby the threshold control circuit (8) has a specifiable threshold voltage (S), which lies above the amplitude of the interference echoes (STE), and is operable to transmit to said distortion circuit (8) such signal amplitudes (NE) which exceed the threshold voltage, and said threshold control circuit being operable to transmit said signal amplitudes (NE) which exceed the threshold voltage true-to-intensity, while the interference echoes are suppressed, a demodulator unit (5) connected with the ultrasonic receiver (2) for receiving the echo signals therefrom and for supplying an output signal (E3), a differentiation stage (16) connected with the demodulator unit (5) for supplying a differentiation signal (E3') which is the output signal (E3) after differentiation by means of said differentiation stage (16), and a mixing stage (15) connected with said distortion circuit (8) and with said differentiation stage (16) for mixing the output signal (E5) of the distortion circuit (8) and the differentiation signal (E3') from the differentiation stage (16), characterized in that said recording device comprises a picture tube (12), and a contrast control means is connected between mixing stage (15) and the picture tube (12) and is responsive to a photographic operation at the picture tube (12) such that the basic luminosity and image contrast is adjusted to the maximum contrast of the film material utilized.

3. Ultrasonic imaging apparatus for ultrasonic-echo recording according to the impulse-echo principle, comprising an ultrasonic receiver which delivers the echo signals with a given dynamic range, an image recording device for the echo signals which manifests a non-linear output/input characteristic, a distortion circuit (8) connected between the ultrasonic receiver (2) and the image recording device (12) which distortion circuit distorts, according to a specifiable pattern, the non-linear characteristic of the recording device (12), in dependence upon a predeterminable optimum dynamic range of the echo signals, and a threshold control circuit (6) connected in series with said distortion circuit (8), and having means whereby the threshold control circuit (8) has a specifiable threshold voltage (S), which lies above the amplitude of the interference ehcoes (STE), and is operable to transmit to said distortion circuit (8) such signal amplitudes (NE) which exceed the threshold voltage, and said threshold control circuit being operable to transmit said signal amplitudes (NE) which exceed the threshold voltage true-to-intensity, while the interference echoes are suppressed, further comprising a contrast control circuit (9) having a contrast adjustment means (10) for controlling echo signal contrast adjustment, said recording device comprising a picture tube (12) having a photographic exposure apparatus coupled therewith including a photographic trigger mechanism for effecting exposure of a film material, said contrast adjustment means (10) being automatically operable in dependence upon the trigger mechanism such that the basic luminosity and image contrast is adjusted to the maximum contrast of the film material utilized.

4. Ultrasonic imaging apparatus according to claim 3, characterized in that in the case of automatic contrast adjustment for a photographic operation by the contrast adjustment means (10), pursuant to increasing the basic luminosity, the contrast adjustment means correspondingly reduces the maximum image contrast.

* * * * *